(12) United States Patent
Chen et al.

(10) Patent No.: US 10,548,534 B2
(45) Date of Patent: Feb. 4, 2020

(54) SYSTEM AND METHOD FOR ANHEDONIA MEASUREMENT USING ACOUSTIC AND CONTEXTUAL CUES

(71) Applicant: Sonde Health, Inc., Boston, MA (US)

(72) Inventors: Michael C. Chen, Norwood, MA (US); Richard K. Jordan, Littleton, MA (US)

(73) Assignee: Sonde Health Inc., Boston, MA (US)

(\*) Notice: Subject to any disclaimer, the term of this patent is extended or adjusted under 35 U.S.C. 154(b) by 31 days.

(21) Appl. No.: 15/464,756

(22) Filed: Mar. 21, 2017

(65) Prior Publication Data

US 2018/0277146 A1 Sep. 27, 2018

Related U.S. Application Data

(60) Provisional application No. 62/310,840, filed on Mar. 21, 2016.

(51) Int. Cl.
*G10L 17/26* (2013.01)
*A61B 5/00* (2006.01)
*A61B 5/16* (2006.01)

(52) U.S. Cl.
CPC ......... *A61B 5/7267* (2013.01); *A61B 5/165* (2013.01); *A61B 5/4803* (2013.01); *A61B 5/7257* (2013.01); *A61B 5/7275* (2013.01); *A61B 2562/0204* (2013.01); *G10L 17/26* (2013.01)

(58) Field of Classification Search
CPC ....................................................... G10L 17/26
See application file for complete search history.

(56) References Cited

U.S. PATENT DOCUMENTS

| | | | | |
|---|---|---|---|---|
| 6,322,503 B1* | 11/2001 | Sparhawk, Jr. | ........ | A61B 5/411 434/236 |
| 2012/0265024 A1* | 10/2012 | Shrivastav | ........... | A61B 5/40 600/300 |
| 2013/0159229 A1* | 6/2013 | Modha | ................ | G06N 3/08 706/16 |
| 2013/0166291 A1* | 6/2013 | Lech | ............... | G10L 17/26 704/232 |
| 2013/0166485 A1* | 6/2013 | Hoffmann | .......... | G06N 99/005 706/20 |
| 2017/0249437 A1* | 8/2017 | Jain | ................. | G16H 50/20 |
| 2017/0372117 A1* | 12/2017 | Bredno | .............. | G06K 9/0014 |

FOREIGN PATENT DOCUMENTS

EP 2712454 A1 * 4/2014

\* cited by examiner

*Primary Examiner* — Feng-Tzer Tzeng
(74) *Attorney, Agent, or Firm* — Ashok Tankha

(57) ABSTRACT

This application provides a system for classifying a status of anhedonia, the system including an audio data collector adapted to collect a sample of speech, and a processing module including an audio feature extractor and a classification unit, wherein the audio feature extractor extracts a plurality of acoustic features from the sample of speech, and the classification unit classifies a status of anhedonia from the plurality of acoustic features.

16 Claims, 10 Drawing Sheets

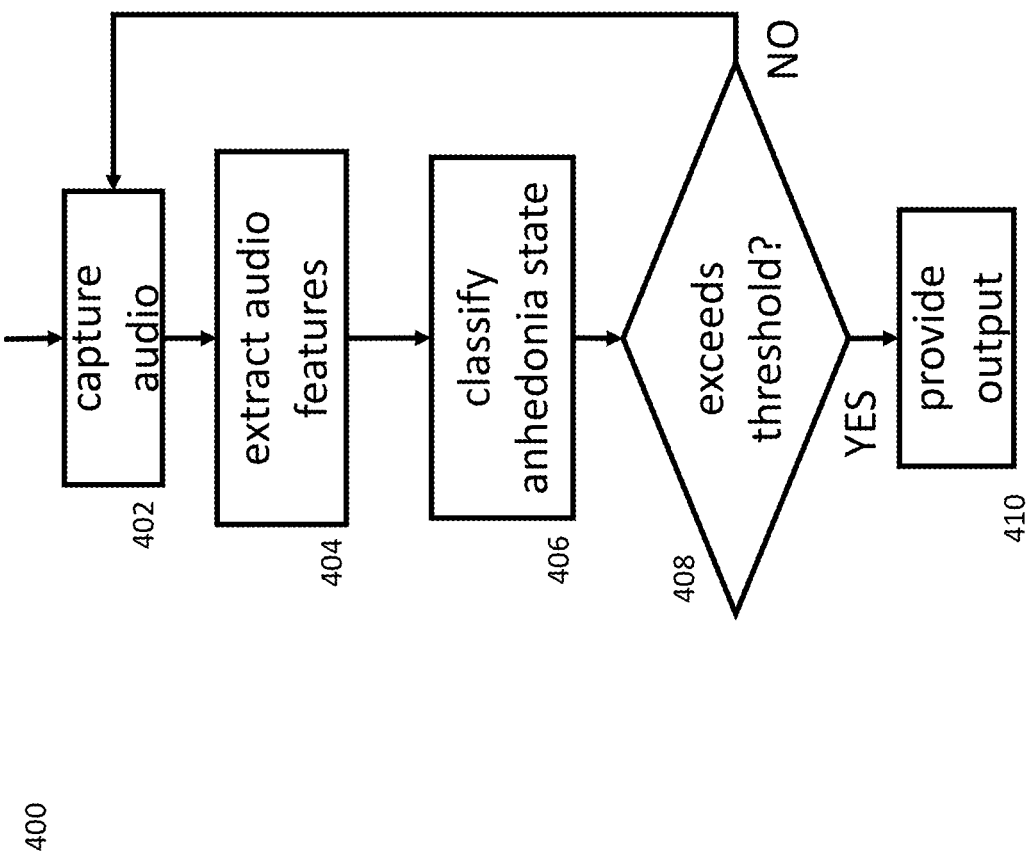

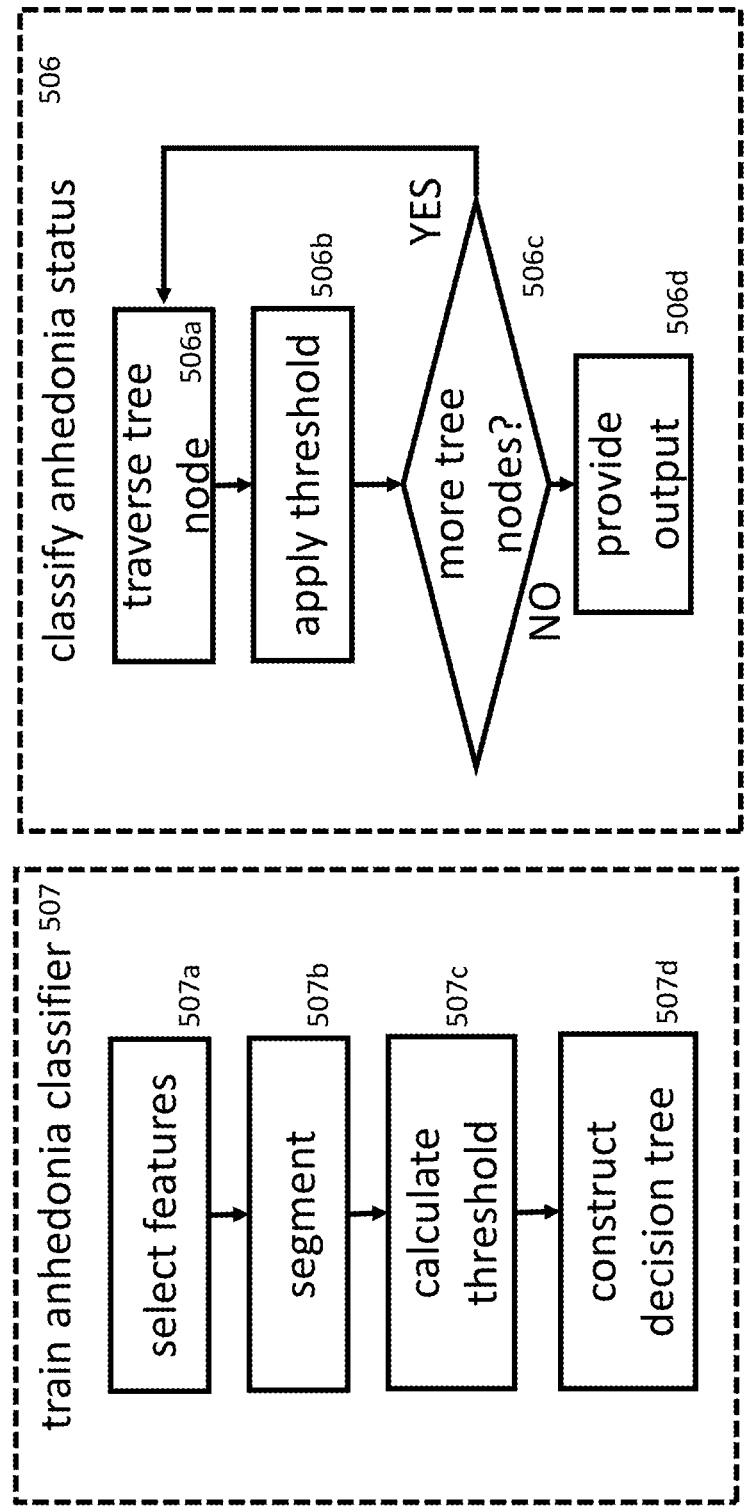

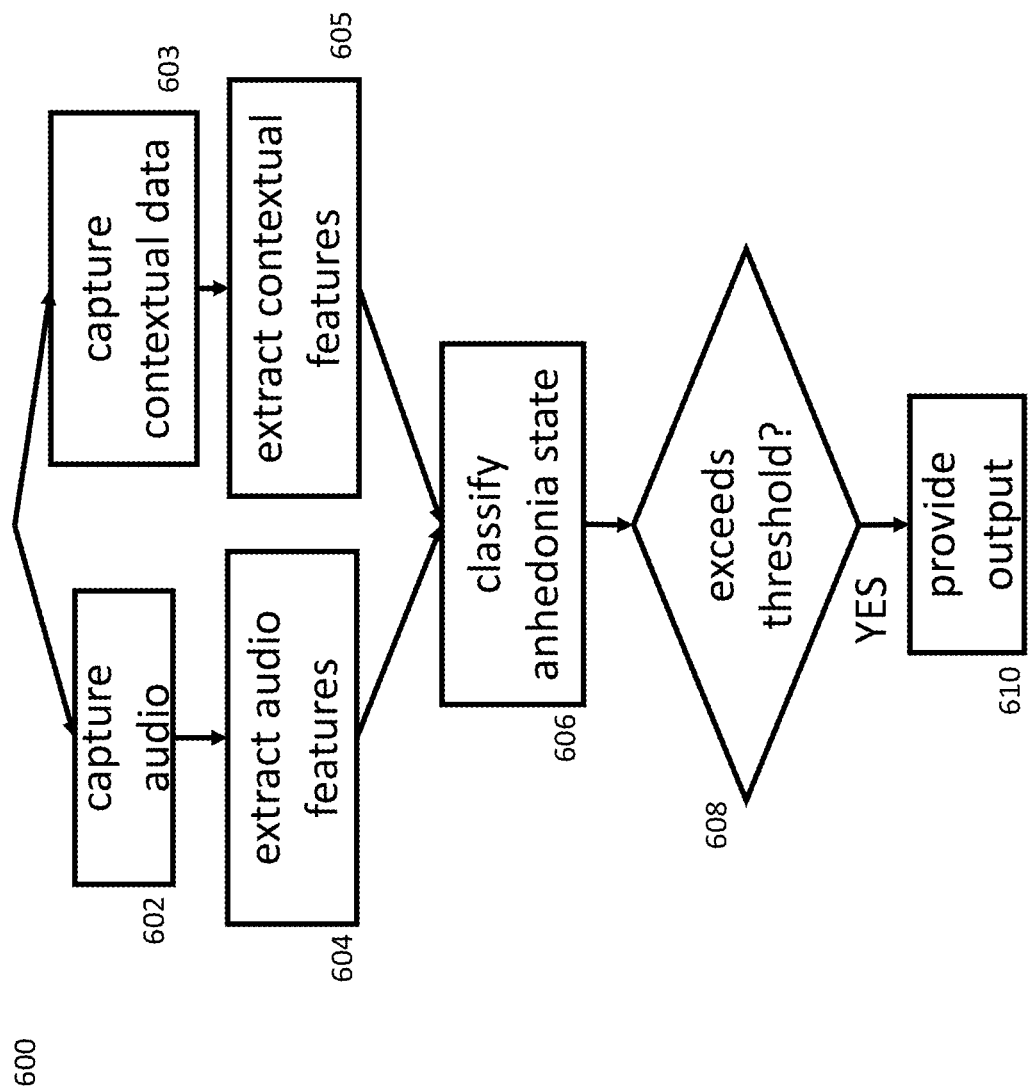

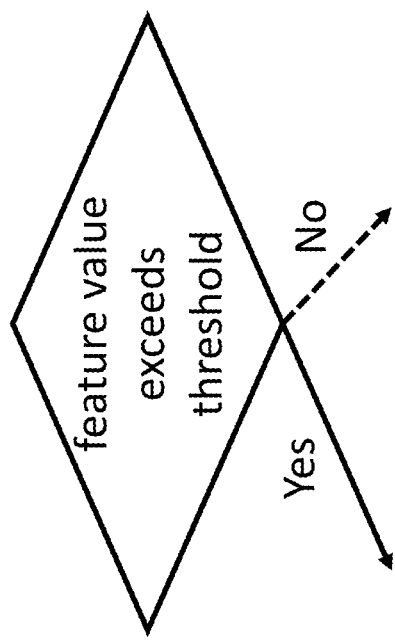
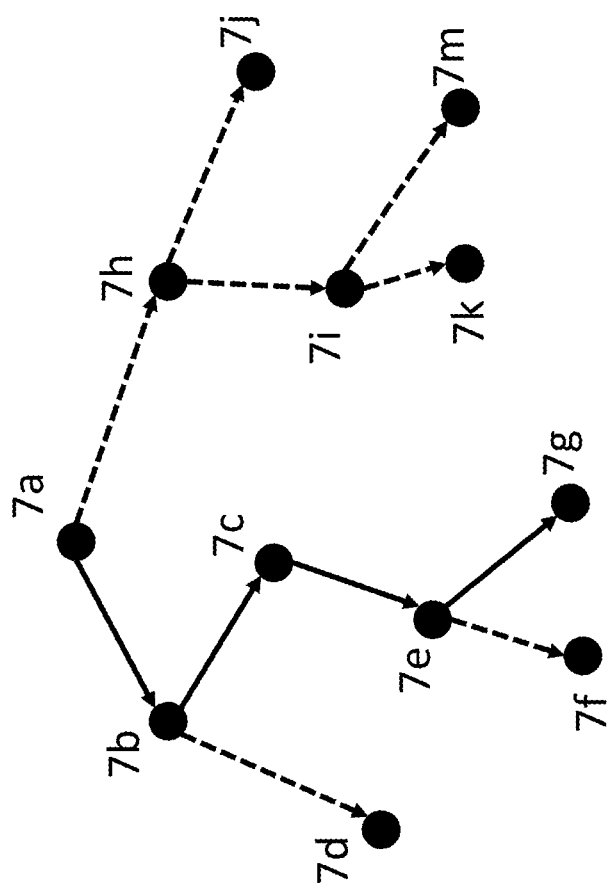

SYSTEM AND METHOD FOR ANHEDONIA MEASUREMENT USING ACOUSTIC AND CONTEXTUAL CUES

CROSS REFERENCE TO RELATED APPLICATIONS

This application claims the benefit of the filing date of U.S. Provisional Patent Application 62/310,840, entitled "SYSTEM AND METHOD FOR ANHEDONIA MEASUREMENT USING NON-LINGUISTIC AND CONTEXTUAL CUES" to Chen et al., which was file on Mar. 21, 2016, the disclosure of which is hereby incorporated entirely herein by reference.

BACKGROUND

Major Depressive Disorder (MDD) is projected to be one of the leading causes of disability in the world. The phenotypic variability of MDD impairs the diagnosis of this disease in large populations and inhibits the development of novel therapies. In addition, symptoms of MDD are not equally ameliorated by treatments such as selective serotonin reuptake inhibitors (SSRIs). Among the symptoms of MDD, anhedonia—defined as diminishment of interest or pleasure in stimuli that were once rewarding—is one of the most common symptoms, occurring in nearly 40% of all MDD cases. It is also one of the most difficult symptoms to treat. Because anhedonia symptoms may predict poor treatment response to overall MDD, methods are needed to specifically detect anhedonia, especially in the context of MDD.

Several barriers exist to the detection, diagnosis, and monitoring of MDD. Most current diagnostic tools for measuring MDD rely on a summation of a constellation of symptoms across days or weeks. These tools are insufficient for detection of specific symptoms, such as anhedonia, as there are typically a small number of questions dedicated to a specific symptom. For example, the Hamilton Depression Rating Scale and Beck Depression Inventory, two commonly used depression instruments, have only one question and four questions, respectively, targeting anhedonia. Furthermore, psychometric studies suggest that anhedonic symptoms and depressive symptoms are only moderately associated.

Common screening instruments do not distinguish between the neuropsychological constructs of anhedonia, consummatory and anticipatory anhedonia. Specifically, consummatory anhedonia describes the loss of momentary pleasure, for example while engaged in an activity that would ordinarily be pleasurable. Anticipatory anhedonia, on the other hand, describes the loss of future pleasure, for example the anticipated amount of pleasure expected from a future activity. Separate measures for these constructs may provide clinically valuable information, as depressed individuals often will have similar consummatory pleasures as non-depressed individuals, but will have impaired anticipatory pleasure. This impairment may affect decision-making, and measuring the subtypes of anhedonia may guide effective treatments.

SUMMARY

Embodiments of the present invention provide systems and methods of assessing anhedonia in a subject. The methods include steps of collecting speech sample with an audio data sensor, with or without additional data from contextual sensors, to extract audio features of voice, speech, or noise, with or without additional contextual features, and to generate a measure of anhedonia in a subject based on classification of at least one audio feature with or without additional contextual features. The systems include an audio data collector adapted to collect a sample of speech and a processing module including an audio feature extractor and a classification unit. The audio feature extractor extracts a plurality of acoustic features from the sample of speech, and the classification unit classifies a status of anhedonia from the plurality of acoustic features.

BRIEF DESCRIPTION OF THE DRAWINGS

FIG. 4 depicts a method for classifying a status of anhedonia according to an embodiment of the present inventions;

FIG. 5A-C depict a method for classifying a status of anhedonia according to an embodiment of the present inventions;

FIG. 6 depicts a method for classifying a status of anhedonia according to another embodiment of the present inventions FIG. 7A-B depict a method for classifying a status of anhedonia according to an embodiment of the present inventions;

DESCRIPTION OF THE INVENTION

Figure 1:
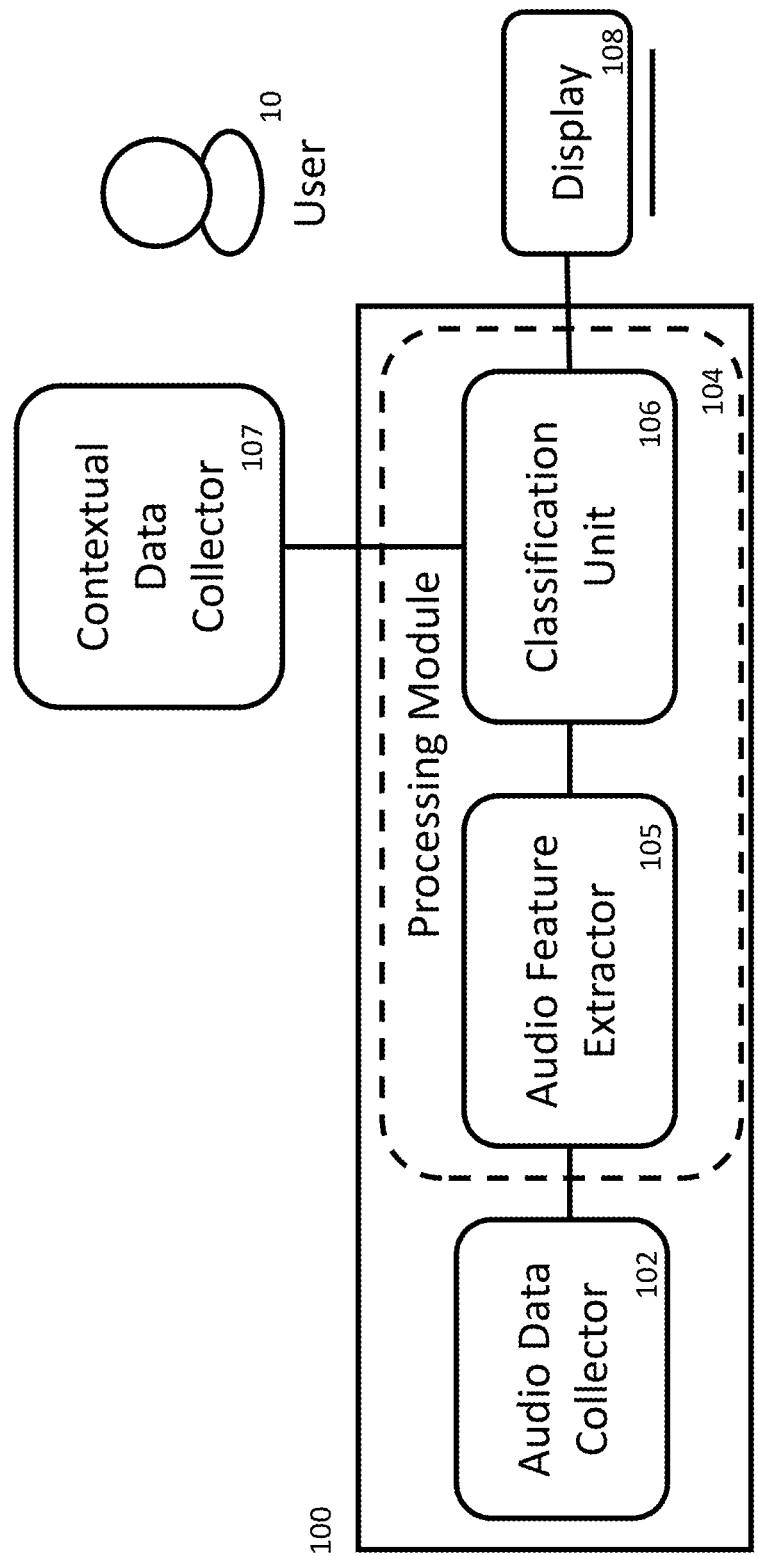
FIG. 1 depicts a system for classifying a status of anhedonia according to an embodiment of the present inventions.

As shown in FIG. 1, an embodiment of the present invention provides a system 100 for classifying a status of anhedonia. The system 100 includes an audio data collector 102 adapted to collect a sample of speech, a processing module 104 including an audio feature extractor 105 and a classification unit 106. The audio feature extractor 105 extracts a plurality of acoustic features from the sample of speech, and the classification unit 106 classifies a status of anhedonia from the plurality of acoustic features.

As shown in FIG. 1, the system 100 can further couple with a contextual data collector 107 and a display 108 to collect additional contextual health data from user 10. The performance of system 100 can be furthermore improved by the contextual data such as those activity measurements obtained from accelerometers, light sensors, screen use and interaction data, and phone call, messaging, or data use.

Embodiments of the present invention provides several advantages over existing MDD screening tools, including the specific determination of the neuropsychological components of anhedonia, consummatory and anticipatory anhedonia. Embodiments of the present invention can also measure anhedonia state within short time periods, compared to traditional screening tools that rely on measurements across weeks. Another advantage is the language-independence of the analysis, as well as the integration of contextual sensor data that allows for additional information. For example, the audio features may help determine an overall score of anhedonia, while contextual cues such as accelerometry may help determine component scores of anhedonia, e.g. anticipatory behavior.

Figure 2:
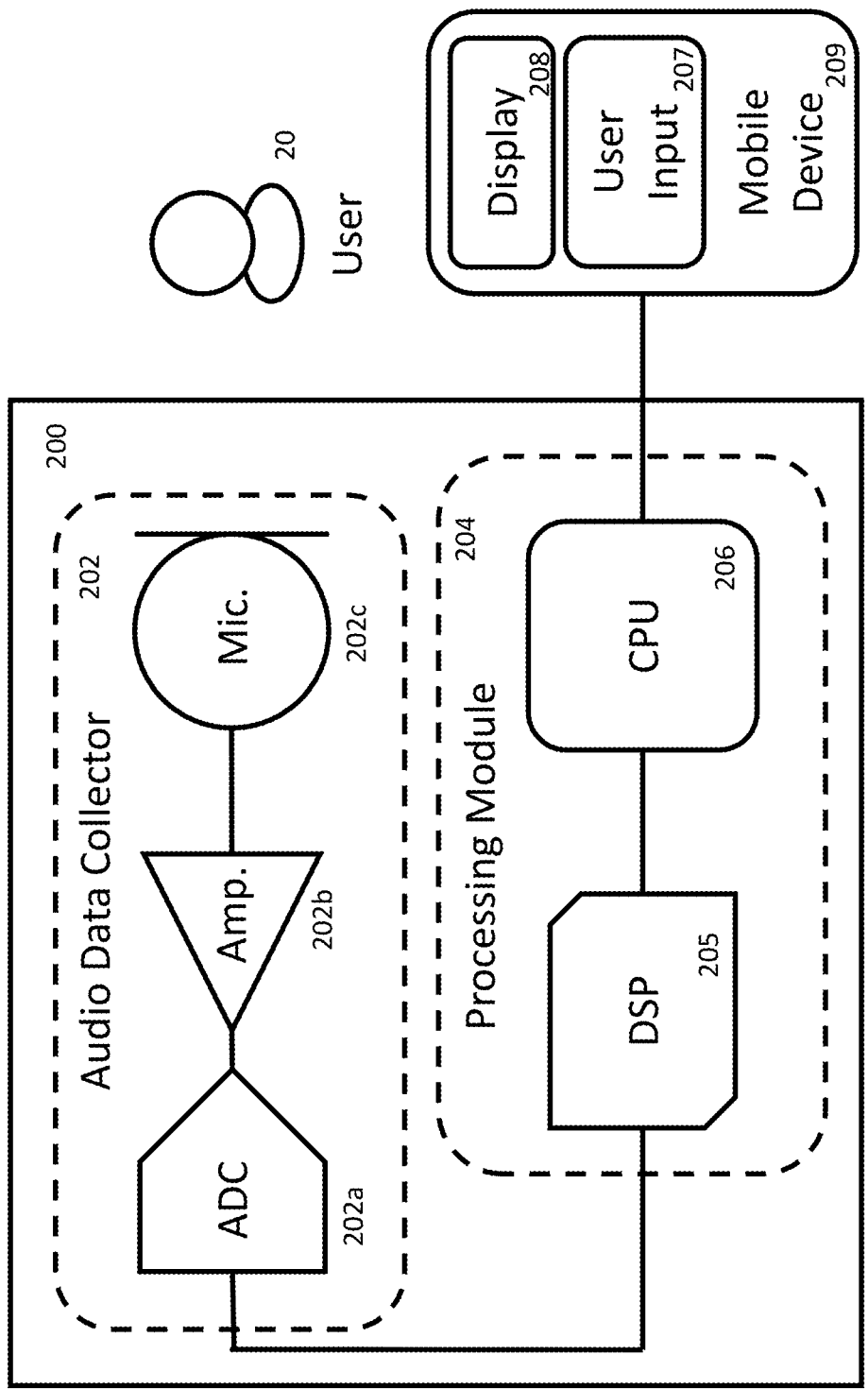
FIG. 2 depicts a system for classifying a status of anhedonia according to another embodiment of the present inventions.

The audio data collector 202 can be embodied with a microphone module, as shown in FIG. 2. According to an embodiment of the present invention, the audio data collector 202 includes a microphone 202c for converting an acoustic energy into a voltage signal. The audio data collector 202 also includes an operational amplifier 202b coupled to the microphone for amplifying the voltage signal. And the audio data collector 202 includes an analog-to-digital converter 202a for converting the voltage signal into digital data.

Also shown in FIG. 2, is an embodiment of the processing module 204. According to an embodiment of the present invention, the processing module 204 includes a digital signal processor 205. The digital signal processor can be coupled to the audio data collector 202 to extract the plurality of acoustic features from the sample of speech. In other words, when the digital signal processor 205 executes a stored instruction set, it performs the functions of the audio feature extractor 105 (see FIG. 1). The processing module also includes a general-purpose processor 206. The general-purpose digital processing can be coupled to an output of the digital signal processor 205 (see audio feature extractor 105 in FIG. 1) to receive the plurality of acoustic features and classifies the sample of speech to a predetermined status of anhedonia. In other words, when the general-purpose processor 206 executes a stored instruction set, it performs the functions of the classification unit 106 (see FIG. 1).

Figure 3:
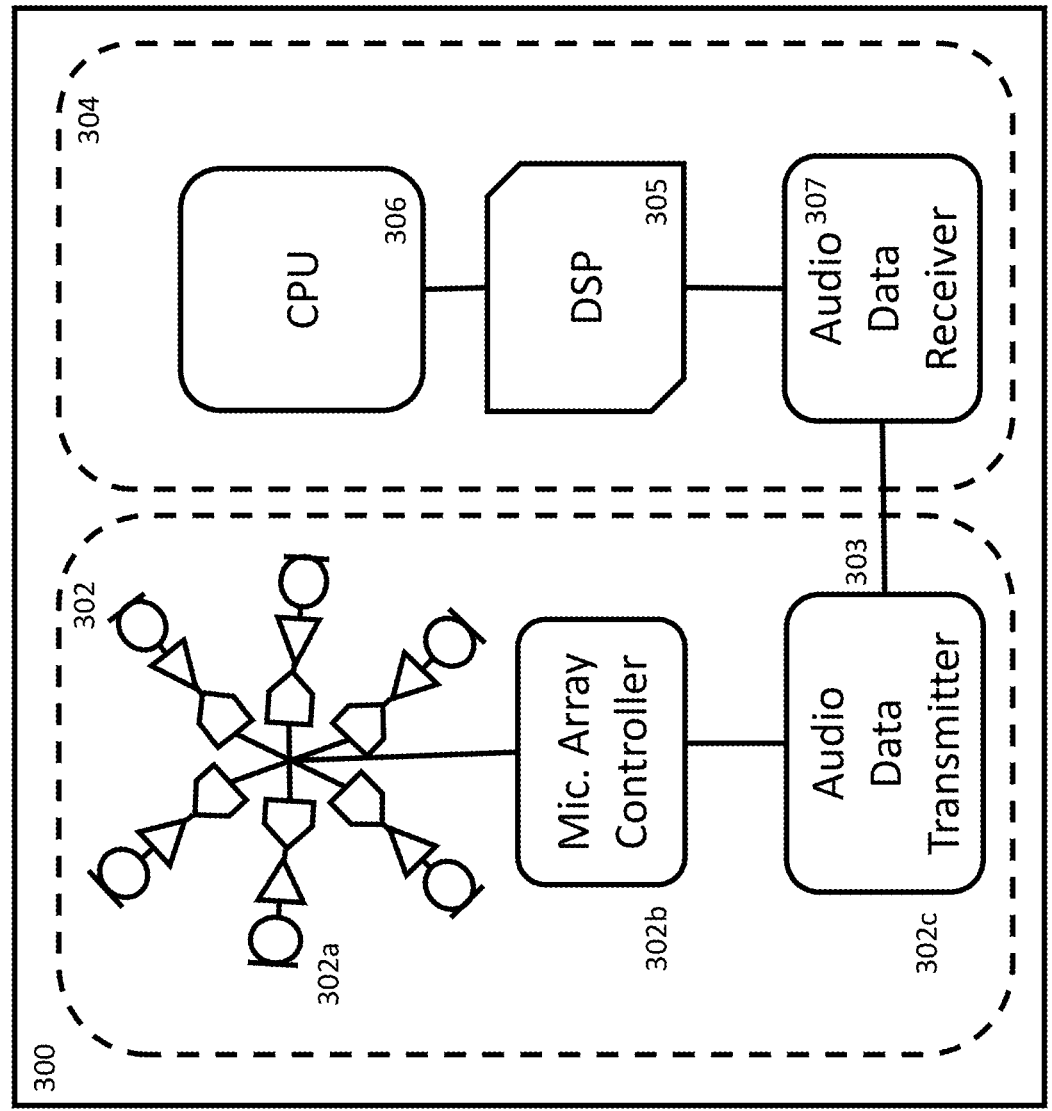
FIG. 3 depicts a system for classifying a status of anhedonia according to another embodiment of the present inventions.

FIG. 3 shows another embodiment of the system 300 for classifying a status of anhedonia. As shown in FIG. 3, the audio data collector 302 can include a plurality of audio signal capture units 302a. This is commonly referred to as an array arrangement of the microphones. Each audio signal capture unit 302a includes a microphone for converting an acoustic energy into a voltage signal, an operational amplifier coupled to the microphone for amplifying the voltage signal and an analog-to-digital converter for converting the voltage signal into digital data. The audio data collector 302 also includes a microphone array controller 302b, which can be adapted to select audio data captured from one or more of the audio signal capture unites 302a. The microphone array controller 302b can also provide the selected audio data to an audio data transmitter 302c. The audio data transmitter 302c can be transmit the digital data across a communication link 303 to the processing module 304. As such, the processing module 304 and the audio data collector 302 can be coupled to communicate across any of a communication bus on a physical device, an internet protocol network, and wireless networks such as a Bluetooth network.

As shown in FIG. 3, the processing module 304 can include audio data receiver 307 for receiving digital data from the audio data transmitter 302c. As shown, the audio data receiver 307 can be coupled to an input of the digital signal processor 305 to provide the digital data for audio feature extraction.

FIG. 4 show a method 400 for classifying a status of anhedonia according to an embodiment of the present inventions. The method includes the step of providing an audio data collector to collect a sample of speech 402, extracting a plurality of acoustic features from the sample of speech 404, and classifying a status of anhedonia from the plurality of acoustic features 406. the plurality of acoustic features extracted includes two or more of feature types including a time domain descriptor, a spectral domain descriptor; and a perceptual model descriptor. The plurality of acoustic features can further include the plurality of acoustic features further comprises one of an autocorrelation a descriptor, a cross-correlation between two descriptors, and a coding coefficient of a descriptor.

According to one embodiment of the method 400, the classified status of anhedonia is either a status of consummatory anhedonia or an anticipatory anhedonia, along with a probability of the classification. As such, if the probability is determined to exceed a predetermined threshold (YES in FIG. 4), in step 408, an output is provided to a user at step 410. According to another embodiment, if the probability of the classification is determined to not have exceed the predetermined threshold (NO in FIG. 4), the method 400 returns to step 402 to capture another speech sample.

According to an embodiment of the present invention, in step 406, a decision tree based method is implemented to perform the classification. An embodiment of the decision tree is described with respect to FIGS. 5A-C below.

In other embodiments, the classification can be performed with other established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Figure 5A:
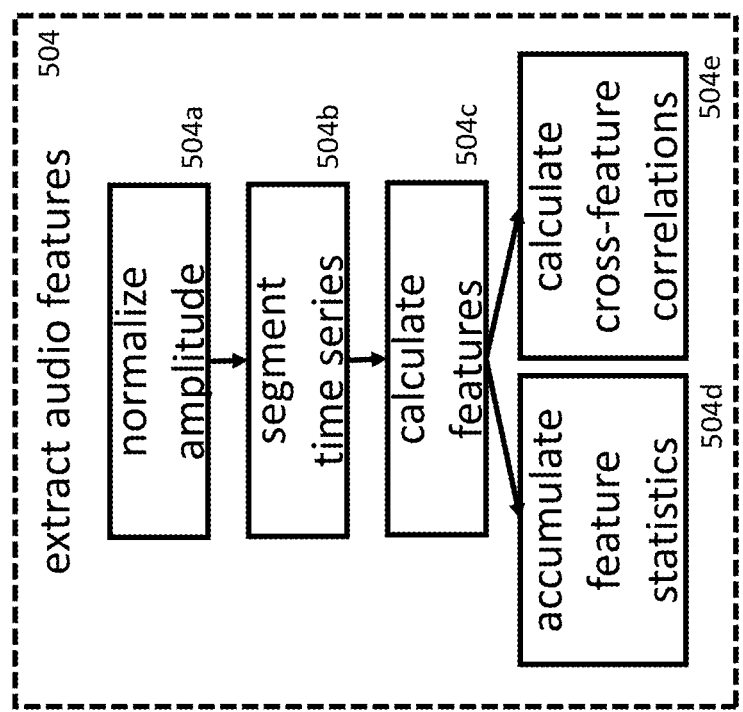
Figure 8B:
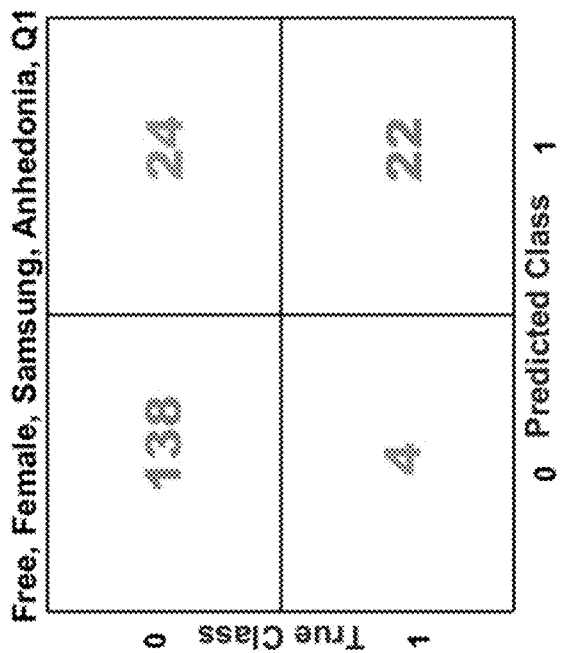
FIG. 8A-B depicts a performance measurement of a method for classifying a status of anhedonia, according to an embodiment of the present inventions.
Figure 8A:
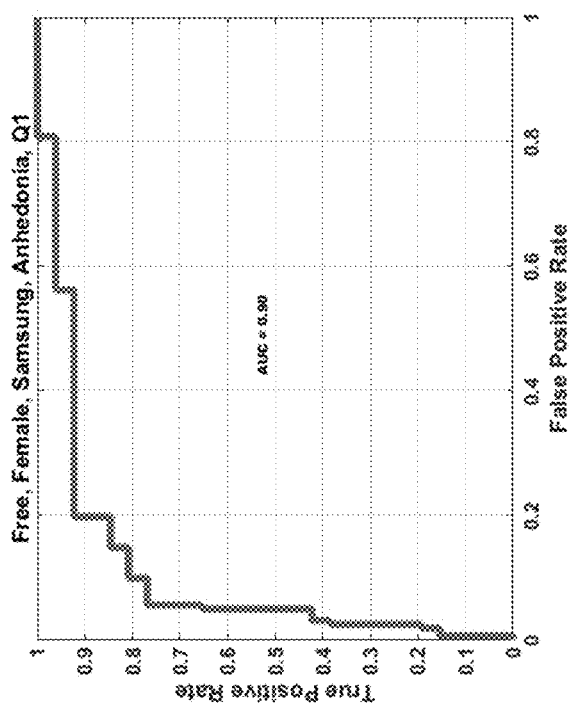
Figure 9B:
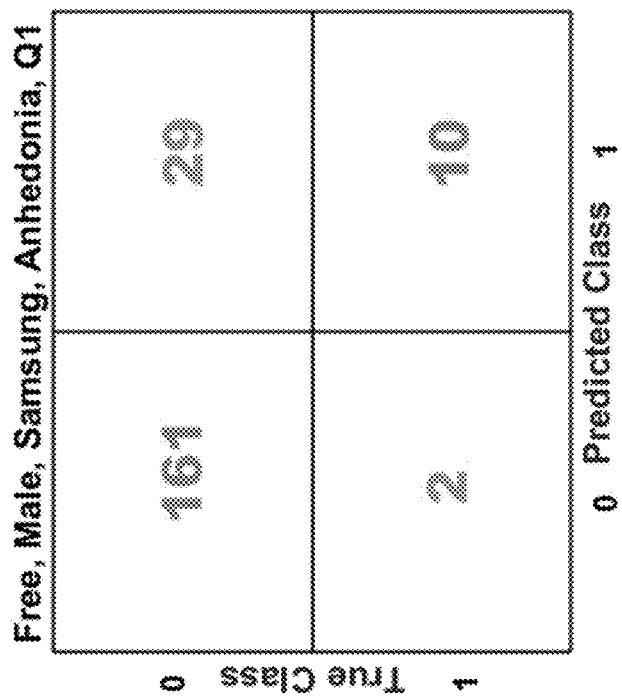
FIG. 9A-B depicts a performance measurement of a method for classifying a status of anhedonia, according to another embodiment of the present inventions.
Figure 9A:
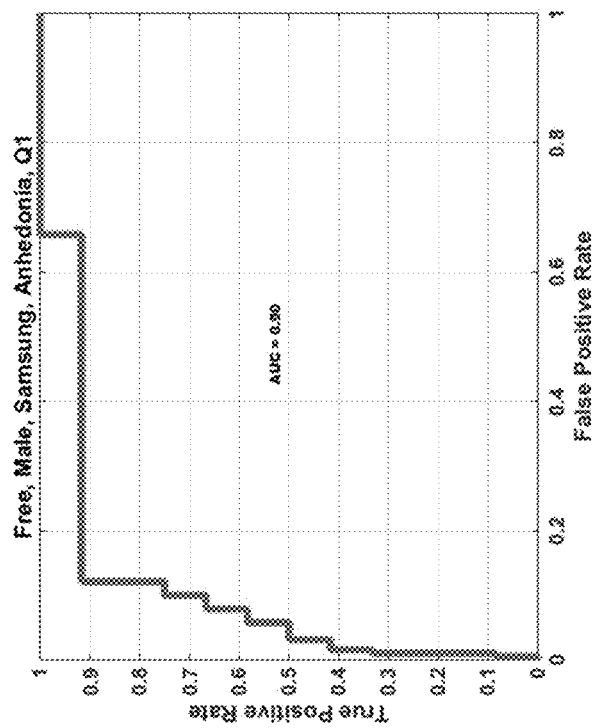

With respect to FIG. 5A, there is provided a detailed example of the step 504 for extracting a plurality of acoustic features for an embodiment of the method 400. In particular, an acoustic feature (acoustic descriptor) can be segmented from a time series of audio data (step 504b). Each acoustic feature can be defined as a feature parameter computed from a short-duration frame $x_k(n)$ having a sample length $N_{sample}$ from an audio signal at time $t=k \cdot T_{sample}$. The length of the frame can be selected to ensure substantial stationarity of the feature parameter within the frame, and to ensure that the frame contains sufficient number of samples n to compute feature parameter with statistical confidence. A typical frame lengths can vary from 10 to 35 ms.

In step 504c, a feature is calculated from a segment of the audio data. In particular, a time domain feature, a spectral or frequency domain feature, or a perceptual model feature can be calculated.

According to one embodiment, a time domain feature can be computed directly from the time domain signal $x_k(n)$, for example, the rate of zero-crossings (ZCR), amplitude statistics, and signal energy. The Zero-Crossing Rate (ZCR) describes the number of sign changes c of $x_k(n)$ per unit of time (typically one second).

$$ZCR=c/1.0\ s$$

A sign change can be defined as when the condition $x(n-1)x(n)<0$ is satisfied.

Similarly, a sign change can be defined as when both conditions $x(n-1)x(n+1)<0$ and $x(n)=0$ are satisfied.

Amplitude statistics such as maximum and minimum signal amplitudes, or the maximum absolute value of the amplitudes can be calculated directly from $x_k(n)$.

Signal energy can be computed directly from $x_k(n)$ as well. Assuming an audio signal to have a mean value of zero, the signal energy E for a signal $x(n)$ with $n \in [0; N-1]$, is defined as the sum of squared amplitudes of the signal x, or $E=\Sigma_{n=0}^{N-1} x^2(n)$.

According to another embodiment, a frequency domain or spectral feature can be computed in step 504c. We can define a general spectrum X(m), which can be a magnitude spectrum $X_M(m)$, a power spectrum $X_P(m)$, power spectral densities in dB, or a band or filterbank spectrum.

With a general spectrum X(m), we can compute a set of frequency domain feature that satisfy a relation $f=F(m)$ and $m=F^{-1}(f)$ between the linear frequency f in Hz and the bin index m.

Most spectral features can be computed from a sub-band range defined by the lower and upper bin indices $m_{lower}$ and $m_{upper}$, i.e. the spectrum spanning the range between $m_{lower}=1$ and $m_{upper}=M$. For a case of constrained sub-band frequency range with lower and upper border frequencies of $f_{lower}$ and $f_{upper}$, the respective integer valued bin indices are $m_{lower}=\lfloor F^{-1}(f_{lower})+0.5 \rfloor$ and $m_{upper}=\lfloor F^{-1}(f_{upper})+0.5 \rfloor$.

Various conventional spectral features can be computed. For example, band energy, spectral slope, flatness, centroid, moments, entropy, and differences can be computed per conventional definitions within the sub-band range as defined above.

Furthermore, a short-duration autocorrelation measure can be calculated within a frame.

The short-time Autocorrelation function (ACF) can provide a high resolution for low frequency periodicities within a frame—the autocorrelation provides a measure of the signal's self-similarity at discrete time lags $\tau \in [-\tau_{max}, \tau_{max}]$.

Furthermore, a Cepstrum can be computed. The Cepstrum can be computed by combining a Fourier transform, its inverse and the natural logarithm function:

$$Cepstrum=FFT^{-1}[\ln(FFT(x) \cdot FFT^*(x))]=FFT^{-1}[\ln(|FFT(x)|^2)]$$

The effect of the natural logarithm is a temporal separation of the source and filter parts of the audio signal x in the Cepstrum.

Pitch of the audio signal can be computed. The estimation of pitch can be approximated by an estimation of the fundamental frequency F0. Where pitch is a perceptual term which refers to the perceived tonality, i.e. by a human listener. Pitch is related to the F0, i.e., the lowest frequency in the harmonic series of the tone. An F0 estimation can be computed by conventional techniques, for example by the RAPT algorithm from David Talkin.

Furthermore, formants or the resonance frequencies of the vocal tract system can be computed, which characterize phonemes such as voiced vowels. They are visible in speech spectra as maxima of the envelope. From this, one method for calculation of formants is by applying a peak-picking algorithm directly to speech power spectra.

Furthermore, a parametrization in the form of Line Spectral Pairs (LSPs) can be computed by conventional techniques. The LSPs are related to the formants of the speech signal, which are estimated from the roots of the polynomial H(z). Precisely, two LSFs enclose a formant as left and right boundaries.

Next, with respect to FIGS. 5B and 5C, there is provide an example implementation of the classifying step 506. The classification function can be provided by either an online or an offline trained classifier. As an illustrative example, FIG. 5B and the following paragraphs provide a procedure to construct an off-line trained classifier.

With respect to FIG. 5B and the step of select features 507a, many common feature selection methodologies can be implemented. In general, the feature selection method is chosen 1) to uncover and account for nonlinear interactions between the features, and 2) to reduce an overfit to data.

Deprioritized by the first consideration are methods based on linear classification models, for example, LASSO. At the same time, the nonlinear interactions between the features can be addressed by tree-based feature selection methods. However, because methods based on individual trees are known to be unstable to minor changes in the data and prone to overfitting, we used a tree-based ensemble approach, Random Forests (RF), for feature selection.

RF consists of a plurality of decision trees. Every node in the decision tree is a condition on a single feature, designed to divide the dataset into two subsets such that similar response values end up in the same subset. The measure based on which the locally optimal splitting condition is chosen is called the Gini impurity. When training a decision tree, it is computed how much each feature decreases the weighted impurity in the tree. For a forest, the impurity decrease from each feature can be averaged and the features are ranked according to this measure.

Generally, we select a small number of the top-ranked features to include in the final classification model. Deciding how many features to select. To help determine this cut-off, and thereby which features to select, we introduce a large number of random features, which are independent of the target variable, i.e. the anhedonia class, and include them among the speech features. Then, only features having importance greater than that of all the random features are selected. This typically results in only a handful of features being selected (on the order of 10-20, depending on the size of the training set, etc.).

According to one embodiment, the following settings for the step of select features 507a: 1) number of trees: 5000, 2) minimum number of cases (individual subjects) at a node: 5, which is the default: 10, 3) number of random features: 100.

With these parameter settings for the step of select features 507a, we have found this to be a sufficient number of random features to provide a feature importance score threshold.

Next, with respect to FIG. 5B, there is provide an example implementation to the method steps to (off-line) train a classifier according to an embodiment of the present invention.

Anhedonia classification can be trained based on an individual's response to Question 1 of the PHQ-9 questionnaire. If an individual answers the question with 2 or above, he/she is considered to be in the positive class, otherwise he/she is in the negative class.

In a typical study population, only about 14% of females are in the positive class and only about 6% or males are in the positive class. This imbalance of classes poses a problem for most standard classification approaches, which seek to minimize overall misclassification cost and, thereby, tend to be biased towards proper classification of the majority class (i.e. standard methods have difficulty predicting the minority class when the data is highly skewed). It is important to achieve high accuracy in predicting both classes.

Conventional methods for imbalanced classification tasks. For example, boosting algorithms can be implemented to build an ensemble of weak classifiers iteratively. During each iteration, example weights are modified with the goal of correctly classifying examples in the next iteration, which were incorrectly classified during the current iteration. All models that are constructed during the boosting process participate in a weighted vote to classify unlabeled examples. This is effective for dealing with class imbalance because the minority class examples are most likely to be misclassified and therefore given higher weights in subsequent iterations. The method we have used accomplishes boosting by resampling, in which the training data is re-sampled according to examples' assigned weights. This resampled data set is used to construct the model for the given iteration.

Data sampling is another common approach used to address class imbalance in classification tasks. This approach balances the classes in the training data by either undersampling (removing examples from the majority class) or by oversampling (adding examples to the minority class). The goal in either case is to is to present the learning algorithm to be used with an equal number of positive and negative classes. Many sampling methods have been proposed in the literature. The simplest such method is random re-sampling. Random oversampling duplicates examples in the minority class until class balance is attained, while random undersampling removes examples from the majority class to achieve class balance.

While undersampling results in a loss of information by deleting examples from the training class, the benefit can be a reduced computational time for model training. No information is lost via oversampling, but the price is increased computational cost. In many cases, little or no predictive accuracy is lost via undersampling and often undersampling performs better than oversampling, so it is preferable to oversampling when computational costs are a consideration.

According to an embodiment of the present invention, a boosting method dealing with imbalanced classes, RUS-Boost is selected as the method to train the anhedonia classifier in step 507. This combines random undersampling (RUS) of the majority class with boosting (boost). The boosting algorithm it uses is AdaBoost, and the weak learners used in each iteration are classification trees.

Next, as shown in FIGS. 7A and 7B, and referencing FIG. 5C, there is provided an example implementation of a step of classifying a status of anhedonia 506. The step 506 further includes a step of determining, in accordance with a statistical distribution of the acoustic features, a sequence of traversal through an acyclic graph of the acoustic features, traversing (506*a*) the acyclic graph by detecting a threshold crossing for each node of the acyclic graph, providing (506*d*) an output at an end of the traverse step, the output being predictive of a status of anhedonia.

According to another embodiment, the state of anhedonia may be classified according to the audio signal data without joining the contextual sensor data.

According to another embodiment, an audio sensor may be embedded into an electronic device such as a mobile phone, computer, or television. The audio sensor interacts with a CPU, memory, etc. to record audio signals from the environment, including speech from a subject.

According to another embodiment, speech samples may be recorded either passively or actively. If recorded passively, the speech recording may be activated by a substantially constantly running program that detects vocal activity and identifies an authorized user. If recorded actively, the user may be prompted to provide input to the audio sensor, either in the form of a notification (visual, audio, tactile) from the electronic device or via other forms of communication (phone call, email, alarm).

Contextual sensors may be embedded into an electronic device such as a mobile phone, computer, or television. The contextual sensors may include accelerometer, light sensor, screen use, telephonic metadata, website use, etc. The contextual sensors interact with a CPU, memory, etc. to record contextual signals from the environment and/or subject.

According to another embodiment, the user may also be prompted to provide active input through the contextual sensors as an additional form of contextual data. This may interact with the active recording of voice or may be solely based on cued engagement with a contextual sensor like touchscreen interaction, accelerometer use, or interacting with a web site.

According to another embodiment, a computing device within an electronic device or a remote server that inputs the data from the audio sensor and contextual data and holds it in internal memory stores.

Speech-related variables may be extracted from the audio signal, either across an entire recording, in sub-frames of the recording, or continuously from incoming audio signal sent to the computing device. Speech-related variables may include mel-frequency cepstral coefficients (MFCCs), first and second-order frame-to-frame MFCCs difference coefficients (delta MFCCs, delta-delta MFCCs), formants, formant tracking, harmonic-noise-ratio (HNR), pitch, pitch slope, pitch tracking, phone boundaries, phone duration, cepstral peak prominence (CPP), and cross-correlations between these variables on frame-to-frame and variable frame duration bases.

According to another embodiment, speech and contextual data may be combined into a data assembly. The features may be weighted based on a prediction method previously demonstrated to predict the features of anhedonia, consummatory and anticipatory anhedonia.

According to another embodiment, the weighted features may be entered into a model, which is instantiated as software code running on the electronic device. The model makes a prediction of overall anhedonia state, based on the weighted features.

According to another embodiment, the method relays corresponding information about the severity of anhedonia. This information may be directly displayed to a first user on the same electronic device used to capture the data, a different electronic device used by the first user, or an electronic device used by a second user as authorized by the first user (e.g. a clinician, other healthcare advisor, employer, school administrator, or family member).

According to another embodiment, the method furthermore activates active and/or passive vocal and/or contextual data collection to specifically measure the features of anhedonia, consummatory and anticipatory anhedonia.

According to another embodiment, the data resulting from the secondary collection may be extracted into features, weighted, and entered into a model, which is instantiated as software code running on the electronic device.

According to another embodiment, the method uses computational techniques to classify one or more states of anhedonia.

According to another embodiment, the method presents corresponding information about the severity of anhedonia sub-symptoms. This information may be directly presented to a user on the same electronic device used to capture the data, a different electronic device used by the user, or an electronic device used by a clinician or other healthcare advisor authorized by the user.

According to another embodiment, the method stores in memory, either on the electronic device or on a remote server, a time series of the overall, consummatory, and/or anticipatory anhedonia metrics.

According to another embodiment, the method presents summary information about the time series of overall, consummatory, and/or anticipatory anhedonia metrics, or the raw time series of such anhedonia metrics, to clinicians, users, or other parties.

What is claimed is:

1. A system for classifying a status of anhedonia, the system comprising:
    an audio data collector adapted to collect a sample of speech;
    a processing module comprising an audio feature extractor and a classification unit;
    said audio feature extractor adapted to extract a plurality of acoustic features from the sample of speech, wherein said plurality of acoustic features extracted comprise:
        an auto-correlated feature;
        a cross-correlated feature; and
        a coding coefficient of a feature;
    a contextual data collector adapted to receive contextual data from one or more contextual sensors;
    said classification unit adapted to classify said status of anhedonia by combining the extracted plurality of acoustic features and said contextual data received from said contextual sensors, wherein a combination of Random Forest and Gini Impurity is used for selecting said extracted acoustic features, wherein said selected acoustic features are weighted and entered into predictive models, wherein said predictive models determine an overall score of anhedonia, and wherein said contextual data determines component scores of anhedonia; and
    a display unit adapted to display said classified status.

2. The system of claim 1, wherein the audio data collector comprises:
    a microphone adapted to convert an acoustic energy into a voltage signal;
    an operational amplifier coupled to the microphone adapted to amplify the voltage signal; and
    an analog-to-digital converter adapted to convert the voltage signal into digital data.

3. The system of claim 1, wherein the audio data collector comprises:
    a plurality of audio signal capture units, wherein each audio signal capture unit comprises:
        a microphone adapted to convert an acoustic energy into a voltage signal;
        an operational amplifier coupled to the microphone adapted to amplify the voltage signal; and
        an analog-to-digital converter adapted to convert the voltage signal into digital data;
    a microphone array controller adapted to select the digital data captured from one or more of said audio signal capture units, and provide the selected digital data to an audio data transmitter; and
    said audio data transmitter adapted to transmit the digital data across a communication link to the processing module.

4. The system of claim 1, wherein the audio feature extractor comprises a digital signal processor, wherein the digital signal processor is coupled to the audio data collector for said extraction of the plurality of acoustic features from the sample of speech, wherein the classification unit comprises a general-purpose processor, and wherein the general-purpose processor is coupled to an output of the audio feature extractor to receive the plurality of acoustic features extracted by the digital signal processor of the audio feature extractor.

5. The system of claim 1, wherein the plurality of acoustic features extracted by the audio feature extractor further comprises two or more feature types, wherein said feature types comprise:
    a time domain feature;
    a spectral domain feature; and
    a perceptual model feature.

6. The system of claim 1, further comprising:
    said classification unit determining a sequence of traversal through an acyclic graph of the acoustic features, in accordance with a statistical distribution of the acoustic features;
    said classification unit traversing the acyclic graph by detecting a threshold crossing for each node of the acyclic graph; and
    said classification unit providing an output, wherein the output is predictive of said status of anhedonia.

7. A method of classifying a status of anhedonia in a human subject, the method comprising:
    collecting a sample of speech from a microphone, by an audio collector;
    extracting a plurality of acoustic features from the collected sample of speech, by an audio feature extractor of a processor module, wherein said plurality of acoustic features extracted comprise:
        an auto-correlated feature;
        a cross-correlated feature; and
        a coding coefficient of a feature;
    receiving contextual data from one or more contextual sensors, by a contextual data collector;
    combining the plurality of acoustic features and the contextual data to classify said status of anhedonia in the human subject, by a classification unit of the processor module, wherein a combination of Random Forest and Gini Impurity is used for selecting said extracted acoustic features, wherein said selected acoustic features are weighted and entered into predictive models, wherein said predictive models determine an overall score of anhedonia, and wherein said contextual data determines component scores of anhedonia; and displaying the classified status, by a display unit.

8. The method of claim 7, further comprising:

converting an acoustic energy into a voltage signal, by a microphone of the audio data collector;

amplifying the voltage signal, by an operational amplifier of the audio data collector, wherein the operational amplifier is coupled to the microphone; and converting the voltage signal into digital data, by an analog-to-digital converter of the audio data collector, wherein the analog-to-digital converter is coupled to the operational amplifier.

9. The method of claim 7, further comprising:

providing a plurality of audio signal capture units, wherein each audio signal capture unit performs the steps comprising:
 - converting an acoustic energy into a voltage signal, by a microphone of the audio data collector;
 - amplifying the voltage signal, by an operational amplifier coupled to the microphone; and
 - converting the voltage signal into digital data, by an analog-to-digital converter coupled to the operational amplifier.

10. The method of claim 7, further comprising:

providing a digital signal processor in said processor module for said extraction of said plurality of acoustic features from the sample of speech; and receiving the plurality of acoustic features extracted by the digital signal processor and classifying the sample of speech to a predetermined status of anhedonia, by the classification unit of the processor module.

11. The method of claim 7, wherein the plurality of acoustic features further comprises two or more feature types, wherein said feature types comprise:

a time domain feature;

a spectral domain feature; and a perceptual domain feature.

12. The method of claim 7, further comprising:

determining, in accordance with a statistical distribution of the acoustic features, a sequence of traversal through an acyclic graph of the acoustic features, by the classification unit;

traversing the acyclic graph by detecting a threshold crossing for each node of the acyclic graph, by the classification unit;

providing an output, by the classification unit, wherein the output is the status of anhedonia.

13. The system of claim 3, wherein the processor module further comprises an audio data receiver adapted to receive the digital data from the audio data transmitter, wherein the audio feature extractor further comprises a digital signal processor coupled to an output of the audio data receiver, wherein the digital signal processor is configured to extract the plurality of acoustic features from the sample of speech, wherein the classification unit comprises a general-purpose processor coupled to an output of the digital signal processor, and wherein the general-purpose processor is configured to receive the plurality of acoustic features from the digital signal processor.

14. The method of claim 9, wherein an audio data receiver in the processor module receives the digital data from the audio data transmitter, wherein a digital signal processor in the processor module coupled to an output of the audio data receiver extracts the plurality of acoustic features from the sample of speech, and wherein a general-purpose processor in the processor module coupled to an output of the digital signal processor receives the plurality of acoustic features from the digital signal processor.

15. The method of claim 7, wherein said contextual sensors comprise one or more of an accelerometer and a light sensor.

16. The system of claim 1, wherein said contextual sensors comprise one or more of an accelerometer and a light sensor.

* * * * *